United States Patent [19]

Aubouy et al.

[11] 4,414,415
[45] Nov. 8, 1983

[54] PROCESS FOR THE MANUFACTURE OF 2,6-DICHLORO-4-NITROANILINE, AND THE COMPOUND OBTAINED BY THIS PROCESS

[75] Inventors: Michel Aubouy, Paris; Pierre Hamel, Cleon; Marc Molin, Neuilly-sur-Marne, all of France

[73] Assignee: Rhone-Poulenc Agrochimie, Lyons, France

[21] Appl. No.: 263,131

[22] Filed: May 13, 1981

[30] Foreign Application Priority Data

Jun. 6, 1980 [FR] France ............... 80 13021

[51] Int. Cl.³ .................................. C07C 85/24
[52] U.S. Cl. ........................ 564/412; 564/441
[58] Field of Search ................ 564/412, 441

[56] References Cited

U.S. PATENT DOCUMENTS

| | | | |
|---|---|---|---|
| 3,396,195 | 8/1968 | Visser | 564/412 |
| 3,396,200 | 8/1968 | George et al. | 564/412 X |
| 3,754,034 | 8/1973 | Crocker | 564/412 |
| 3,890,388 | 6/1975 | Schimelpfenig | 564/412 |

FOREIGN PATENT DOCUMENTS

| | | | |
|---|---|---|---|
| 507950 | 12/1954 | Canada | 564/412 |
| 51540 | 6/1966 | Poland | 564/412 |

OTHER PUBLICATIONS

Flurscheim, "J. Chem. Soc.", vol. 93, pp. 1,772–1,775 (1908).

*Primary Examiner*—John Doll
*Attorney, Agent, or Firm*—Robert E. Burns; Emmanuel J. Lobato; Bruce L. Adams

[57] ABSTRACT

(1) Process for the manufacture of 2,6-dichloro-4-nitroaniline.

(2) This process consists in chlorinating paranitroaniline, with chlorine gas, in an aqueous solution of hydrochloric acid having a concentration of between 4 and 7.5 N, at the boil, at a temperature between 95° and 110° C.

(3) This process makes it possible to obtain 2,6-dichloro-4-nitroaniline with an improved yield and an improved quality of product.

5 Claims, No Drawings

PROCESS FOR THE MANUFACTURE OF 2,6-DICHLORO-4-NITROANILINE, AND THE COMPOUND OBTAINED BY THIS PROCESS

The present invention relates to a new process for the manufacture of 2,6-dichloro-4-nitroaniline.

This compound is known especially as an intermediate for 3,5-dichloroaniline, which is itself used for the manufacture of various plant-protection products, in particular fungicides.

The preparation of 2,6-dichloro-4-nitroaniline by the chlorination of para-nitroaniline with the aid of chlorine gas, in an aqueous hydrochloric acid medium, was first studied by Flurscheim (compare J. Chem. Soc. 93, 1,772–5 (1908). This study shows that, when the reaction is carried out in the cold and in a moderately concentrated medium (1.8 N), the yield is low (37%), but that it can be substantially increased by carrying out the reaction at the boil and in a dilute hydrochloric acid medium (0.25 N).

This laboratory technique was referred to in numerous subsequent references pertaining to processes of a more industrial nature. In addition to or in place of the hydrochloric acid, these processes use another strong acid, such as sulphuric acid or acetic acid, or also an auxiliary solvent. However, these processes do not have an adequate yield, they give a product of mediocre quality or they present problems of separation and recovery for the purpose of recycling the mother liquors.

However, as the demand for 2,6-dichloro-4-nitroaniline is rising, it is becoming increasingly necessary to find an industrial manufacturing process, i.e. a process which produces a product of good quality, in particular of good filterability, under conditions which cause less pollution.

The object of the present invention is to provide a process which is improved and simplified compared with the techniques of the prior art. The invention also relates to the particular form of the product obtained by this process.

More precisely, the invention relates to a process for the manufacture of 2,6-dichloro-4-nitroaniline by the chlorination, with chlorine gas, of para-nitroaniline in an aqueous solution of hydrochloric acid, at the boil, wherein the reaction is carried out at a temperature of 95° to 110° C., the concentration of hydrochloric acid in the medium being between 4 and 7.5 N and preferably between 4.5 and 6 N.

This reaction is carried out in accordance with the equation:

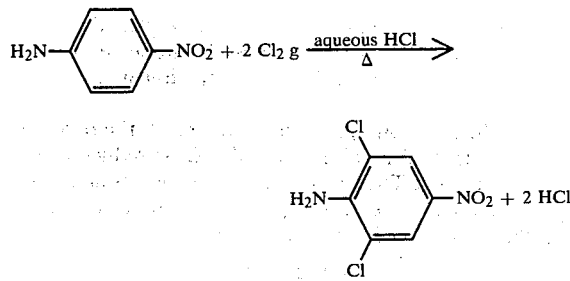

Under the reaction conditions, the para-nitroaniline is very soluble in the medium. A suspension is obtained in the cold, and this is dissolved by heating to the chosen temperature. A stream of chlorine is then introduced into the reactor by means of a dip tube, the temperature being kept approximately constant. The amount of chlorine used is generally at least the stoichiometric amount. A smaller amount reduces the yield. An excess does not reduce the yield but does not improve it. In practice, the reaction is carried out with stoichiometric amounts, but an exess of e.g. up to 50 mol %, relative to the stoichiometric amount, is also suitable.

The starting concentration of hydrochloric acid in the medium must be below saturation, i.e. it must be chosen between 4 and 7.5 N and preferably between 4.5 and 6 N. In fact, it has been found that, in contrast to the teaching of the prior art, a concentrated hydrochloric acid medium (in combination with a high temperature) favours the production of a high yield. The reaction is preferably carried out with a concentration of one mol of amine per liter of hydrochloric acid. Since the reaction itself produces two mols of hydrochloric acid, the normality of the medium increases by about two units during the reaction if no degassing takes place. Now, the medium must not become supersaturated at the end of the reaction; otherwise, the excess acid degases and opposes the transfer of the chlorine towards the liquid, which increases the reaction time. It is for this reason that, with the normality of saturation being about 9.5 N, the concentration of hydrochloric acid in the medium at the start of the reaction will be at most 7.5 N.

Furthermore, a concentration of less than 4 N is not advantageous because the yield then drops below about 75%, which is inadequate for an industrial process.

Another characteristic of the process according to the invention is to carry out the reaction at a high temperature, namely from 95° to 110° C., in practice at the b.p. of the medium, which depends on the chosen concentration of hydrochloric acid. In fact, it has been found that, under these conditions, not only are high yields obtained but also the product obtained is of excellent filterability, which considerably shortens the time required for separating off the 2,6-dichloro-4-nitroaniline. In particular, the best results are obtained for temperatures between 105° and 110° C., which approximately corresponds to the b.p. of the azeotrope of the hydrochloric acid/water mixture. The size of the crystals decreases with the temperature, the lower limit being at about 95° C if it is not desired to increase the reaction time considerably.

According to another embodiment of the invention, the reaction can be carried out with an overpressure. A slight overpressure, in particular, accelerates the transfer of the chlorine into the solution. It has been observed that an overpressure of e.g. 0.26 bar makes it possible to reduce the chlorination time by a factor of 4 to 5, at 110° C. in 6 N starting hydrochloric acid. It is also possible to carry out the reaction in an autoclave at a higher pressure, with or without degassing.

The 2,6-dichloro-4-nitroaniline, which is insoluble under the reaction conditions, precipitates rapidly and progressively until the end. The precipitate is filtered off. The mother liquors essentially consist of an aqueous solution of hydrochloric acid which is more concentrated than the starting solution. By simpledilution with water, they can thus be used immediately for the further operation. The precipitate is then washed and isolated in the customary manner.

The product obtained is in the form of large crystals having an average size of between 100 and 300 microns under the conditions used for the reaction. For the purpose of the invention, the term "average size" is understood as meaning the average of the largest dimensions of the crystals in a sample. This particular form is new because the crystals of the same product obtained by the known processes of chlorination in an aqueous medium have an average size which is about ten times smaller and have twice the moisture content. This form makes it possible to lower the moisture content of the filtered product. This explains why the product according to the invention possesses a remarkable filterability, which makes it possible to increase the productivity of a given manufacturing plant considerably.

Apart from this product, the precipitate contains small amounts of the isomer 2,4-dichloro-6-nitroaniline and small amounts of the monchlorinated derivative, namely 2-chloro-4-nitroaniline, which are not usually separated off because they can be used, or are not troublesome, in the subsequent conversion to 3,5-dichloroaniline. The crude yields can be greater than 90%, and those of 2,6-dichloro-4-nitroaniline are greater than 80% and can reach 90%.

Apart from the good yields and the excellent filterability of the product, the process according to the invention exhibits other advantages, such as the ease with which the chlorination is carried out, the temperature maintaining itself by means of the reflux, the virtually total cessation of the absorption of chlorine at the end of the reaction, which prevents over chlorination, the absence of consumption of hydrochloric acid because of the recycling of the mother liquors, without the need to add fresh acid, and finally the reduction in the effluents, which are restricted to the wash waters.

The following examples illustrate embodiments of the process according to the invention.

EXAMPLE 1

A mixture of 1 liter of 4.5 N hydrochloric acid per mol of para-nitroaniline (138 g) is introduced into a reactor fitted with a reflux condenser and with a gas absorption column packed with sodium hydroxide. The suspension is stirred and heated to about 105° C., and a stream of chlorine is introued into the apparatus by means of a dip tube, the temperature being kept at about 105° C. After about 15 minutes, a precipitate appears and gradually thickens. After about 2 hours, the chlorine flow is progressively reduced until it is no longer absorbed. About 2.2 mols of chlorine are thus introduced per mol of amine, over a total period of 3 to 4 hours.

The mixture is cooled to about 70°–80° C. and filtered, and the product is washed with water. The mother liquors from filtration are kept for preparing the batches for the following operation. The wash waters are discharged.

190.5 g of dry product are obtained per mol of para-nitroaniline introduced. Yield=92%.

Analysis of the product obtained indicates:
82% of 2,6-dichloro-4-nitroaniline,
1.5% of 2,4-dichloro-6-nitroaniline and
5% of 2-chloro-4-nitroaniline.

The crystals have an average size of about 150–200 microns, which represents about 10 times the size of the crystals obtained by chlorination under the usual conditions. Likewise, the specific resistance of the cake, which is characteristic of the filterability, is reduced by a factor of 5 to 10, compared with the other processes of chlorination in an aqueous medium.

The moisture content of the filtered and washed product is 20 to 25%, compared with 40–45% under the usual chlorination conditions.

EXAMPLE 2

The mother liquors originating from the filtration of the preceding operation, i.e. about 0.75 liter of approximately 6 N hydrochloric acid per mol of amine introduced, are made up with water to give 1 liter of 4.5 N hydrochloric acid.

The chlorination takes place in this mixture as in Example 1. The recycling operation is repeated at least ten times without affecting the yield and the quality of the product obtained.

EXAMPLE 3

The procedure of Example 1 is followed, but 6 N hydrochloric acid is introduced, and the chlorination is carried out at a temperature of 95° C. The product is isolated as in Example 1. 196.7 g of dry product are obtained. Yield=95%. Analysis of the product obtained indicates:
88% of 2,6-dichloro-4-nitroaniline,
2% of 2,4-dichloro-6-nitroaniline and
4% of 2-chloro-4-nitroaniline.

EXAMPLE 4

The procedure of Example 1 is followed, except that 6 N hydrochloric acid is introduced and the mixture is heated to 110° C., this being the b.p. of the HCl/water azeotrope. The concentration of acid remains approximately constant as a consequence of the evolution of hydrogen chloride. A crude product is obtained with a yield of 88.5%, the yield of 2,6-dichloro-4-nitroaniline being 83.8%. The crystals of product have an average size of 150 to 200 microns. An increase in the chlorination time, which can be attributed to the evolution of hydrogen chloride, can be noted in this case.

EXAMPLE 5

The procedure of Example 1 is followed and the chlorination is carried out at a temperature of 110° C., a slight pressure of the order of 0.3 bar being maintained in the apparatus. This overpressure can easily be established and maintained by degassing the hydrogen chloride formed through a barometric hydrochloric acid column of appropriate height (about 2.5 m).

The chlorination time is thus reduced to less than 3 hours. The product is isolated as in Example 1, with the same results.

EXAMPLE 6

In this example and the following examples, the chlorination is carried out in a closed autoclave, which makes it possible to perform the reaction under pressure.

With the same charges as for Example 1, the time for introduction of the chlorine at 105° C. is reduced to 1 hour 30 minutes. The pressure in the apparatus increases up to 3 bars at the end of the chlorination. After cooling, the product is isolated as in Example 1.

EXAMPLE 7

After the hydrochloric acid has been introduced as 7.5 N acid, the chlorination is carried out by introducing chlorine at 110° C. When the pressure reaches 3 bars, part of the hydrogen chloride is degassed to about 2 bars and the chlorine feed is resumed. The chlorination is complete in less than 2 hours 30 minutes. The apparatus is cooled and brought back to atmospheric pressure by purging the gas formed. After filtration and washing, 182 g of product containing:
- 90% of 2,6-dichloro-4-nitroaniline,
- 2.5% of 2,4-dichloro-6-nitroaniline and
- 1% of 2-chloro-4-nitroaniline are collected (yield: 88%).

We claim:

1. A process for the manufacture of 2,6-dichloro-4-nitroaniline by the chlorination, with chlorine gas, of para-nitroaniline in an aqueous solution of hydrochloric acid, at the boil, wherein the reaction is carried out at a temperature of 95° to 110° C., the concentration of hydrochloric acid in the medium being between 4 and 7.5 N.

2. A process according to claim 1, wherein the reaction is carried out at 105°–110° C., the concentration of hydrochloric acid in the medium being between 4.5 and 6 N.

3. A process according to claim 1, which comprises carrying out the reaction with an overpressure.

4. The process according to claim 3 in which the reaction is carried out at an overpressure of about 0.26 to 3 bars.

5. The process according to any one of claims 1 to 3 in which the reaction is carried out at a concentration of about one mol of para-nitroaniline per liter of said aqueous solution of hydrochloric acid.

* * * * *